United States Patent
Chen et al.

(10) Patent No.: US 9,167,816 B2
(45) Date of Patent: Oct. 27, 2015

(54) ANTIMICROBIAL COMPOSITION FOR INHIBITING MICROBIAL ORGANISMS AND THE METHOD THEREOF

(71) Applicant: National Taiwan University, Taipei (TW)

(72) Inventors: Chao-Ying Chen, Taipei (TW); Chia-Hua Lin, Taipei (TW); Min-Wei Chang, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 14/622,125

(22) Filed: Feb. 13, 2015

(65) Prior Publication Data
US 2015/0230466 A1    Aug. 20, 2015

Related U.S. Application Data (63) Continuation-in-part of application No. 13/963,432, filed on Aug. 9, 2013.

(51) Int. Cl.
*A01N 47/44*    (2006.01)
*A01N 43/50*    (2006.01)

(52) U.S. Cl.
CPC ...................... *A01N 43/50* (2013.01)

(58) Field of Classification Search
CPC ....... A01N 37/46; A01N 65/42; A01N 43/50; C07K 14/415
USPC ...................... 514/2.3, 2.4, 2.8, 3.3
See application file for complete search history.

(56) References Cited

PUBLICATIONS

Pelegrini et al., "Antibacterial Peptides fromPlants:What They Are and How They ProbablyWork", Biochemistry Research International, Jan. 13, 2011, 9 pages, vol. 2011.
Montesinos, "Antimicrobial peptides and plant disease control", MINIREVIEW, Mar. 2007, 11 pages, vol. 270.
Brandenburg et al., "Antimicrobial Peptides: Multifunctional Drugs for Different Applications", Polymers, 2012, pp. 539-560, vol. 4.
Brogden, "Antimicrobial Peptides: Pore Formers or Metabolic Inhibitors in Bacteria?", Feb. 10, 2005, pp. 238-250, vol. 3.
Rahnamaeian, "Antimicrobial peptides Modes of mechanism, modulaton of defense responses", Plant Signaling & Behavior, Sep. 2011, pp. 1325-1332, 6:9.
Brucker et al., "Apoptosis-inducing antifungal peptides and proteins", Biochem. Soc. Trans., 2011, pp. 1527-1532, vol. 39.
Chen, et al., "Induced host resistance against Botrytis leaf blight", Advances in Plant Disease Management, 2003, pp. 259-267.
Kessmann et al., "Induction of Systemic Acquired Disease Resistance in Plants by Chemicals", Annu. Rev. Phytopathol., 1994, pp. 439-459, No. 32.
Lu et al., "Molecular analysis of lily leaves in response to salicylic acid effective towards protection against Botrytis elliptica", Plant Science, Mar. 17, 2005, 9 pages, vol. 169.
Hammami et al., "PhytAMP: a database dedicated to antimicrobial plant peptides", Nucleic Acids Research, Oct. 4, 2008, pp. D963-D968, vol. 37.
Stotz et al., "Plant defensins Defense, development and application", Plant Signaling & Behavior, Nov. 2009, pp. 1010-1012, 4:11.
Lu et al., "P robenazole-Induced Resistance of Lily Leaves agaist Botrytis elliptica", Plant Pathology Bulletin, 1998, pp. 134-140, No. 7.
Alvarez, "Salicylic acid in the machinery of hypersensitive cell death and disease resistance", Plant Molecular Biology, 2000, pp. 429-442, No. 44.
Bostock, "Signal conflicts and synergies in induced resistance to multiple attackers", Physiological and Molecular Plant Pathology, May 1999, pp. 99-109, No. 55.
Lu, "Stomatal closure, callose deposition, and increase LsGRP1-corresponding transcript in probenazole-induced resistance against Botrytis elliptica in lily", Plant Science, Jan. 19, 2007, pp. 913-919, No. 172.
Durrant et al., "Systemic Acquired Resistance", Annu. Rev. Phytopathol., Mar. 26, 2004, pp. 185-209, No. 42.
Sticher et al., "Systemic Acquired Resistance", Annu. Rev. Phytopathol., 1997, pp. 235-270, No. 35.
Van Loon et., "Systemic Resistance Induced by Rhizosphere Bacteria", Annu. Rev. Phytopathol., 1998, pp. 453-483, No. 36.
Micro-organisms. Last Retrieved Mar. 22, 2014, from http://www.le.ac.uk/se/centres/sci/selfstudy/eco7.htm.
Chia-Hua Lin et al., "A Potent Antimicrobial Peptide Derived from the Protein LsGRP1 of *Lilium*", Phytopathology, Apr. 2014, vol. 104, No. 4, pp. 340-346.

*Primary Examiner* — James H Alstrum Acevedo
*Assistant Examiner* — Tara Martinez
(74) *Attorney, Agent, or Firm* — Muncy, Geissler, Olds & Lowe, P.C.

(57) ABSTRACT

The invention relates to a method of controlling or combating microbial organism by applying an antimicrobial peptide to the microbial organisms, wherein said antimicrobial peptide derived from *Lilium* 'Stargazer' glycine-rich protein 1. In addition, the present invention provides an antimicrobial composition comprising an antimicrobial peptide of the invention, an additional biocidal agent and pharmaceutically acceptable vehicles, excipients, diluents, and adjuvants.

4 Claims, 9 Drawing Sheets

LsGRP1 (accession number: AAL61539.1)

| | LsGRP1-derived peptide | | |
|---|---|---|---|
| Prediction server | LsGRP1^N | LsGRP1^G | LsGRP1^C |
| AMPA | + | + | + |
| APD2 | --- | +/− | + |
| AntiBP2 | --- | --- | + |
| CAMP | --- | + | +/− |
| ClassAMP | + | + | + |

ANTIMICROBIAL COMPOSITION FOR INHIBITING MICROBIAL ORGANISMS AND THE METHOD THEREOF

CROSS-REFERENCE TO RELATED APPLICATIONS

This application is a Continuation-in-Part of application Ser. No. 13/963,432, filed on Aug. 9, 2013, and now for which the benefit is claimed under 35 U.S.C §120; the content of each of the above-mentioned patent application is hereby incorporated by reference herein in its entirety and made a part of this specification.

BACKGROUND OF THE INVENTION

1. Field of the Invention

The present invention relates to a method of controlling or combating microbial organism. The invention also relates to an antimicrobial composition for inhibiting microbial organism.

2. Description of the Prior Art

Antimicrobial peptides (AMPs) are natural antibiotics that act as a primary defense barrier to prevent the invasion of pathogenic microorganisms in living organisms. Recently, scientific studies have disclosed a class of naturally occurring antimicrobial peptides in humans, mammals, plants, insects and other organisms. Generally these peptides have a net positive charge (i.e., cationic), and it is believed that the antimicrobial efficacy of theses peptides is attributed to their ability to penetrate and disrupt the microbial membranes, thereby killing the microbe or inhibiting its growth.

Plant AMPs are 3-10 kDa cationic peptides that exhibit a high content of cysteine and/or glycine residues. These plant AMPs are expressed constitutively or are induced following pathogen attack, and most are localized in extracellular matrix. The structures of plant AMPs are generally stabilized by cysteine-linked intramolecular disulfide bridges, which ensure the effective interaction of AMPs with microbial plasma membranes and lead to disruption of membrane integrity of the microorganisms (Pelegrini et al. 2011; Hammam et al. 2009). In addition to membrane permeabilization, other antimicrobial mechanisms of AMPs have been proposed, such as the suppression of nucleic acid and protein synthesis, inhibition of enzymatic activity, and induction of programmed cell death (Brogden, 2005; De Brucker et al. 2011; Rahnamaeian, 2011). Because AMPs exhibit diverse modes of action and broad-spectrum antimicrobial activity, they are highly recommended candidates for drug development and plant disease control (Brandenburg et al. 2012; Montesinos, 2007; Stotz et al. 2009).

Induced resistance in plants refers to a state with enhanced defenses in response to biotic and abiotic stress (Bostock, 1999; Sticher et al. 1997; van Loon et al. 1998; Durrant and Dong, 2004). The plant hormone salicylic acid is a disease resistance modulator involved in defensive signaling and stimulates the expression of numerous defense genes in many plant systems (Alvarez, 2000; Kessmann et al. 1994). LsGRP1 (*Lilium* 'Stargazer' glycine-rich protein 1) is a defense-related gene of lily that is differentially expressed post-treatments with salicylic acid and probenazole and after inoculation with *Botrytis elliptica* (Berk.) Cooke. LsGRP1 is predicted to encode a glycine-rich protein of 138 amino acids (a.a.) containing a 23-a.a. N-terminal signal peptide, which targets the mature protein to the plasma membrane or extracellular matrix. The deduced LsGRP1 sequence shares greater than 53% similarity with various plant GRPs and has a highly conserved domain structure, including an N-terminal signal peptide, a central glycine-rich domain and a C-terminal cysteine-rich domain (Chen et al. 2003; Lu and Chen, 2005; Lu et al. 1998, 2007).

However, to date there have not been any reports to identify the antimicrobial activity of LsGRP1-derived peptides. There is a need in the art to explore the great potential of LsGRP1-derived peptides for antimicrobial application.

Reference Cited [Referenced By]

Other Reference

Alvarez M E (2000) Salicylic acid in the machinery of hypersensitive cell death and disease resistance. Plant Mol. Biol. 4:429-442.

Bostock R M (1999) Signal conflicts and synergies in induced resistance to multiple attackers. Physiol. Mol. Plant Pathol. 55:99-109.

Brandenburg L-O, Merres J, Albrecht L-J, Varoga D, Pufe T (2012) Antimicrobial peptides: Multifunctional drugs for different applications. Polymers 4:539-560.

Brogden K A (2005) Antimicrobial peptides: Pore formers or metabolic inhibitors in bacteria? Nat. Rev. Microbiol. 3:238-250.

Chen C Y, Lu Y Y, Chung J C (2003) Induced host resistance against *Botrytis* leaf blight. In Huang, H., C. and Acharya, S., N. (Eds), Advances in plant disease management (pp. 259-267). Management. Research Signpost, Trivandrum, Kerala, India.

De Brucker K, Cammue B P A, Thevissen K (2011) Apoptosis-inducing antifungal peptides and proteins. Biochem. Soc. Trans. 39:1527-1532.

Durrant W E, Dong X (2004) Systemic acquired resistance. Annu Rev. Phytopathol. 42:185-209.

Hammami R, Ben Hamida J, Vergoten G, Fliss I (2009) PhytAMP: a database dedicated to antimicrobial plant peptides. Nucleic Acids Res. 37:963-968.

Kessmann H, Staub T, Hofmann C, Maetzke T, Herzog J, Ward E, Uknes S, Ryals J (1994) Induction of systemic acquired resistance in plants by chemicals. Annu Rev. Phytopathol. 32: 439-459.

Lu Y Y, Chen C Y (1998) Probenazole-induced resistance of lily leaves against *Botrytis elliptica*. Plant Pathol. Bull. 7:134-140.

Lu Y Y, Chen C Y (2005) Molecular analysis of lily leaves in response to salicylic acid effective towards protection against *Botrytis elliptica*. Plant Sci. 169:1-9.

Lu Y Y, Liu Y H, Chen C Y (2007) Stomatal closure, callose deposition, and increase of LsGRP1-corresponding transcript in probenazole-induced resistance against *Botrytis elliptica* in lily. Plant Sci. 172:913-919.

Montesinos E (2007) Antimicrobial peptides and plant disease control. FEMS Microbiol. Lett. 270:1-11.

Pelegrini B P, Del Sarto R P, Silva O N, Franco O L, Grossi-de-Sa M F (2011) Antibacterial peptides from plants: what they are and how they probably work. Biochem. Res. Int. 2011:250349.

Rahnamaeian M (2011) Antimicrobial peptides: Modes of mechanism, modulation of defense responses. Plant Signal. Behav. 6:1325-1332.

Sticher L, Mauch-Mani B, Métraux J P (1997) Systemic acquired resistance. Annu Rev. Phytopathol. 35: 235-270.

Stotz H U, Thomson J G, Wang Y (2009) Plant defensins: Defense, development and application. Plant Signal Behav. 4:1010-1012.

van Loon L C, Bakker P A H M, Pieterse, C M J (1998) Systemic resistance induced by rhizosphere bacteria. Ann. Rev. Phytopathol. 36: 453-483.

SUMMARY OF THE INVENTION

In the first aspect the invention relates to a method of controlling or combating microbial organisms, comprising applying an antimicrobial peptide to the microbial organism, such as fungal organisms or bacteria, wherein said antimicrobial peptide is selected from the group consisting of LsGRP1$^N$ (SEQ ID NO:1), LsGRP1$^G$ (SEQ ID NO:2), LsGRP1$^C$ (SEQ ID NO:3), and peptide with at least 90% sequence similarity to sequences of LsGRP1$^N$, LsGRP1$^G$, and LsGRP1$^C$.

In the second aspect the present invention relates to an antimicrobial composition comprising, as an active ingredient, an antimicrobial peptide of the invention, which may further comprise an additional biocidal agent and pharmaceutically acceptable vehicles, excipients, diluents, and adjuvants.

The antimicrobial peptide of the present invention can be used to treat any target microbial organism. For example, the target microbial organism of the present invention can be any bacteria or fungi. In one embodiment, the target microbial organism is a gram-positive bacterium, such as *Bacillus subtilis* 28-4. In another embodiment, the target microbial organism is a gram-negative bacteria, such as *Pseudomonas syringae* pv. *syringae* 61, *Agrobacterium tumefaciens* C58C$^1$, *Escherichia coli* DH5α, *Dickeya chrysanthemi* TA1 and *Xanthomonas campestris* XCP3. In yet another embodiment, the target microbial organism is a fungus, such as *Alternaria brassicicola* Ac1, *Botrytis cinerea* B134, *Botrytis elliptica* B061, *Colletotrichum acutatum* HL1, or *Colletotrichum gleosporioides* MT1.

In general, the antimicrobial peptide of the present invention can be used to treat a target microbial organism at any place, e.g., at a plant surface, and at any tissue including surfaces of any implant.

Furthermore, the antimicrobial peptide of the present invention can be used in a wound healing composition or hygiene products, such as bandages, anti-dandruff hair products, and wet wipe.

BRIEF DESCRIPTION OF THE DRAWINGS

FIG. 2 shows analysis of antimicrobial activity of LsGRP1-derived pepides. (A) Bacterial growth inhibited by LsGRP1-derived peptides. The bacterial suspension with an OD$_{600}$ of 0.15 was treated with 2.5 mg/ml peptide solution for 90 min, and the CFUs in each peptide sample were measured at 20-24 h post treatment by serial-dilution plating Inhibition of bacterial growth (%)=[(CFUs in water treatment−CFUs in peptide treatment)/CFUs in water treatment]×100%. (B) Spore germination of plant fungal pathogens inhibited by LsGRP1-derived peptides. Fungal spores with a concentration of 1×10$^5$ spores/ml were treated with 2.5 mg/ml peptide for 16-20 h before the observation of spore germination under light microscope. Inhibition of fungal spore germination (%)=[(Number of spores germinating in water−Number of spores germinating in peptide solution)/Number of spores germinating in water]×100%.

FIG. 4 shows effect of LsGRP1$^C$ on plant fungal pathogens. The fungal spores (A) and hyphae (B) were treated with 50 μg/ml LsGRP1$^C$ for 2 h and 16 h, respectively. Then membrane permeability, chromatin condensation and reactive oxygen species accumulation of treated spores and hyphae were assayed by staining with SYTOX Green, DAPI and H$_2$DCFDA, respectively. Sterile deionized water was used instead of LsGRP1$^C$ as a control. Bar=20 μm (A) or 50 μm (B).

DETAILED DESCRIPTION OF THE PREFERRED EMBODIMENT

In the first aspect the present invention relates to a method of controlling or combating microbial organisms, comprising applying an antimicrobial peptide to the microbial organism, wherein said antimicrobial peptide exhibits antimicrobial activity, such as antifungal activity and antibacterial activity and is selected from the group consisting of LsGRP1$^N$ (SEQ ID NO:1), LsGRP1$^G$ (SEQ ID NO:2), LsGRP1$^C$ (SEQ ID NO:3), and peptide with at least 90% sequence similarity to sequences of LsGRP1$^N$, LsGRP1$^G$, and LsGRP1$^C$.

In a preferred embodiment, the antifungal activity is the activity for inhibiting the growth of fungus, wherein the fungus is selected from the group consisting of *Alternaria bras-*

*sicicola* Ac1, *Botrytis cinerea* B134, *Botrytis elliptica* B061, *Colletotrichum acutatum* HL1, and *Colletotrichum gleosporioides* MT1.

In another preferred embodiment, the antibacterial activity is the activity for inhibiting the growth of bacterium, wherein the bacterium is selected from the group consisting of *Agrobacterium tumefaciens* C58C$^1$, *Bacillus subtilis* 28-4, *Escherichia coli* DH5α, *Dickeya chrysanthemi* TA1, *Pseudomonas syringae* pv. *syringae* 61, or *Xanthomonas campestris* XCP3.

The term "antimicrobial peptide" is intended to comprise the linear as well as the active folded structures of the polypeptide, and may be used interchangeably with the term "antimicrobial protein".

The term "antimicrobial activity" means in the context of the present invention that the polypeptide of the invention is active in controlling or combating microbial organisms, including fungal organisms, such as filamentous fungi, and/or bacterial organisms, such as gram-positive and gram-negative bacteria. Suitable assays for assessing whether a polypeptide has antimicrobial activity include but not limit to the ones described in the "Antibacterial assay" and "Antifungal assay" sections.

The present invention also relates to an antimicrobial composition comprising, an antimicrobial peptide of the invention, which may further comprise an additional biocidal agent and pharmaceutically acceptable vehicles, excipients, diluents, and adjuvants.

The invention will now be further illustrated by the following examples. However, it should be noted that the scope of present invention is not limited by the examples provided herein.

EXAMPLE 1

1. Computational Analysis

The antimicrobial activity of LsGRP1$^N$, LsGRP1$^G$ and LsGRP1$^C$ deduced from LsGRP1 sequences (NCBI accession number: AAL61539.1) were analyzed using AMP prediction servers AMPA (Torrent et al. 2009), APD2 (Wang and Wang, 2004; Wang et al. 2009), AntiBP2 (Lata et al. 2007), CAMP (Thomas et al. 2010) and ClassAMP (Joseph et al. 2012)

2. Results

Figure 1:
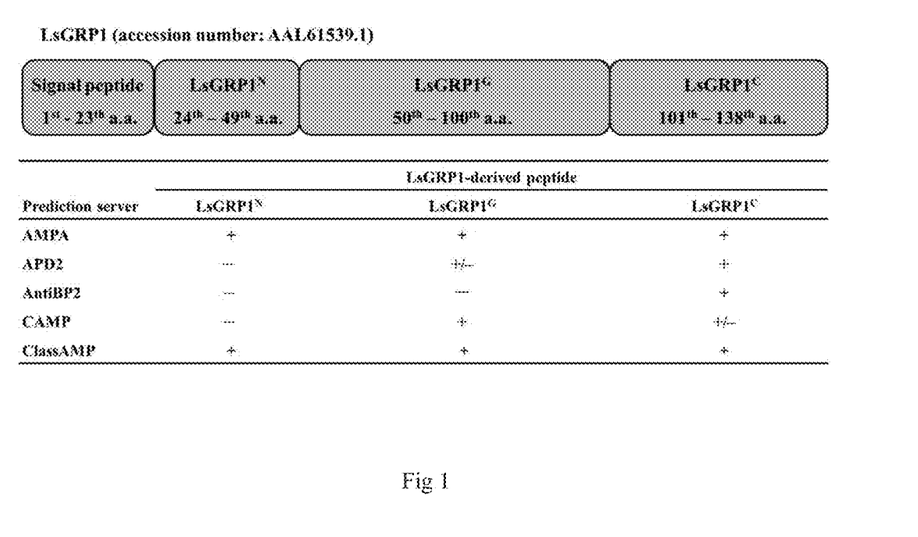
FIG. 1 shows schematic pattern and antimicrobial activity predition of LsGRP1-derived peptides. LsGRP1$^N$, LsGRP1$^G$ and LsGRP1$^C$ are indicated on different blocks of the deduced LsGRP1 sequence. The antimicrobial activity of LsGRP1-derived peptides predicted by server AMPA (Torrent et al. 2009), APD2 (Wang et al. 2009), AntiBP2 (Lata et al. 2007), CAMP (Thomas et al. 2010) and ClassAMP (Joseph et al. 2012) was shown below. A putative antimicrobial activity was predicted (+) or not predicted (−). "+/−" indicates an ambiguous result predicted by the server.

LsGRP1$^N$, LsGRP1$^G$ and LsGRP1$^C$ were assayed for antimicrobial activity using different AMP prediction servers (FIG. 1). LsGRP1$^C$ possessing antimicrobial activity was suggested by five servers used whereas antimicrobial potentials of LsGRP1$^N$ and LsGRP1$^G$ were only predicted by two and four servers, respectively. Therefore, LsGRP1$^C$ might be the main part of LsGRP1 interfering the expression of LsGRP1 in *E. coli* system.

EXAMPLE 2

1. Preparation of LsGRP1-Derived Peptides

LsGRP1$^N$, LsGRP1$^G$ and LsGRP1$^C$ were chemically synthesized by Genscript USA Inc. with purities greater than 90% after purified by high performance liquid chromatography using a solvent system composed with the mixture of acetonitrile, trifluoroacetic acid and water. The identity of synthetic peptides was confirmed by electrospray ionization mass spectrometry. Synthetic peptides and bovine serum albumin (BSA, Sigma-Aldrich) were all dissolved in sterile deionized water at a concentration of 10 mg/ml and stored at −20° C. before use.

2. Microorganisms

The bacterial strains used in this invention included *Agrobacterium tumefaciens* C58C$^1$ (Van Larebeke et al., 1974), *Bacillus subtilis* 28-4, *Escherichia coli* DH5α (Invitrogen), *Dickeya chrysanthemi* TA1, *Pseudomonas syringae* pv. *syringae* 61 (Huang et al., 1988), and *Xanthomonas campestris* XCP3. These bacterial strains were cultured on Luria-Bertani (LB) media (1% tryptone, 0.5% yeast extract, 1% NaCl, 1.5% agar) and 523 media (1% sucrose, 0.8% casein hydrolysate, 0.4% yeast extract, 0.2% KH$_2$PO4, 0.00358% MgSO$_4$, 1.5% agar, pH 7.0). The incubation temperature for *E. coli* DH5α and the other bacterial strains were 37° C. and 28° C., respectively. For antibacterial assay, bacterial strains were incubated in 3 ml LB broth at 180 rpm for 12-16 h and diluted to an experimental concentration using sterile deionized water.

The fungi used in this study included *Alternaria brassicicola* Ac1, *Botrytis cinerea* B-134, *Botrytis elliptica* B061, *Colletotrichum acutatum* HL1, and *Colletotrichum gleosporioides* MT1. The *B. elliptica* B061 was cultured on V-8 medium (20% V-8 vegetable juice [Campbell Soup Company, Camden, N.J., U.S.A.], 0.3% CaCO$_3$, and 1.5% agar) at 20° C. for 5-8 days whereas the other fungi were cultured on potato dextrose agar (Difco Laboratories, Detroit, Mich., U.S.A.) at 25° C. for 7-10 days. Spore suspensions of different fungal strains were prepared in sterile deionized water and diluted to an experimental concentration.

3. Growth Inhibition Assay

The antibacterial and antifungal activities of these peptides were determined by measuring the inhibition rate of bacterial growth and fungal spore germination. Bacterial suspensions with an OD$_{600}$ at 0.15 were treated with peptide solution for 90 min, then serially diluted and plated on LB media. After incubation for 20-24 h, the colony-forming units (CFUs) in each peptide-treated sample were quantified. The inhibition of bacterial growth (%)=[(CFUs in water treatment−CFUs in peptide treatment)/CFUs in water treatment]×100%. On the other hand, fungal spore suspensions of 1×10$^5$ spores/ml were treated with peptide solutions for 16-20 h, and then the spore germinations were examined under microscope. The germ tube greater than two times of spore length was considered germinated Inhibition of fungal spore germination (%)= [(Number of the spores germinating in water−Number of the spores germinating in peptide solution)/Number of the spores germinating in water]×100%. Sterile deionized water replaced the peptide solution as a control treatment. All assays were performed in triplicate. Based on the data, the concentrations of peptide for 50% growth inhibition (IC$_{50}$) of each microbe were determined.

4. Results (1) Antibacterial Activity of LsGRP1-Derived Peptides

Figure 2:
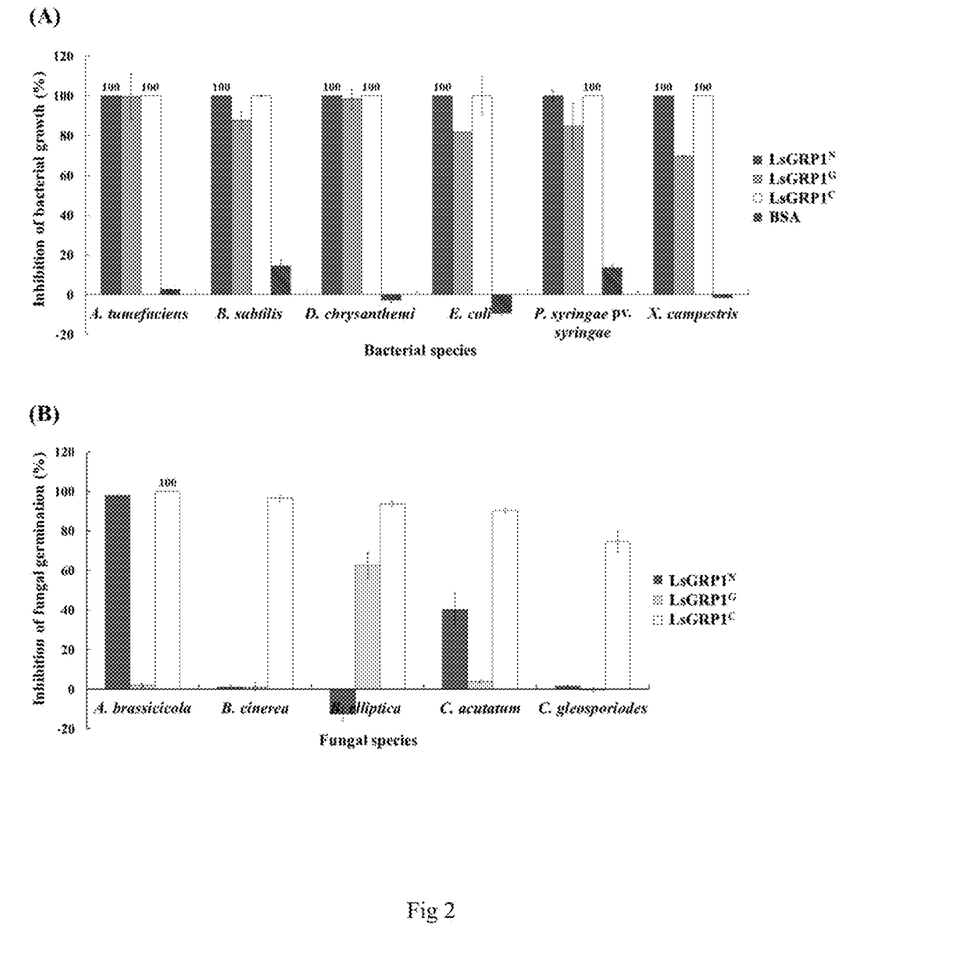

In antibacterial assay, the growths of six bacterial species was significantly inhibited in the presence of 2500 µg/ml LsGRP1-derived peptides but not inhibited by BSA solution (FIG. 2A); thus, these synthetic peptides were considered to have antibacterial activities. Both LsGRP1$^N$ and LsGRP1$^C$ caused more than 99.5% growth inhibition on all assayed bacterial species whereas LsGRP1$^G$ had a lower inhibitory activity. Although LsGRP1$^G$ caused over 98.5% inhibition on the growth of *A. tumefaciens* C58C$^1$ and *D. chrysanthemi* TA1, the inhibitory effects of LsGRP1$^G$ were lower on *B. subtilis* 28-4 (87.6%), *E. coli* DH5a (81.8%), *P. syringae* pv. *syringae* 61 (84.8%) and *X. campestris* XCP3 (69.6%). Thus, LsGRP1$^N$ and LsGRP1$^C$ exhibited higher antibacterial activities and broader spectrum as compared with LsGRP1$^G$.

(2) Antifungal Activity of LsGRP1-Derived Peptides

The antifungal activities of the LsGRP1-derived peptides were investigated by measuring the inhibition rate of spore germination, and LsGRP1$^C$ exhibited the highest antifungal activity and broadest spectrum (FIG. 2B). LsGRP1$^C$ inhibited spore germination by greater than 90% in four fungal strains, *A. brassicicola* Ac1, *B. cinerea* B-134, *B. elliptica* B061 and *C. acutatum* HL1, while the inhibition rate of spore germination in *C. gleosporioides* MT1 was 74.7%. On the other hand, LsGRP1$^N$ inhibited spore germinations on *A. brassicicola* Ac1 and *C. acutatum* HL1 by 98.0% and 40.3%, respectively; however, the spore germination of *B. cinerea* B-134 and *C. gleosporioides* MT1 were not affected. Worthy of notice, LsGRP1$^N$ slightly enhanced spore germination of *B. elliptica* B061 (−12.4% inhibition). In contrast to LsGRP1$^N$ and LsGRP1$^C$, LsGRP1$^G$ did not inhibit spore germination with the exception of *B. elliptica* B061 (62.7% inhibition). Hence, LsGRP1$^C$ is more potent to be an antimicrobial peptide as compared with LsGRP1$^N$ and LsGRP1$^G$.

EXAMPLE 3

LsGRP1$^C$ Exhibited Effective Inhibitory Activity on Different Kinds of Bacterial and Fungal Species To further demonstrate the antimicrobial activity of LsGRP1$^C$, the IC$_{50}$ values of LsGRP1$^C$ on different bacterial and fungal species were determined (Table 1). The IC$_{50}$ values of LsGRP1$^C$ on assayed microbes were all below 86.13 μg/ml, in an effective range of antimicrobial peptide. The IC$_{50}$ values of LsGRP1$^C$ on all assayed bacterial species were lower than 32.19 μg/ml except on *A. tumefaciens* C58C$^1$ (IC$_{50}$=71.79 μg/ml), and *E. coli* DH5α was most sensitive to LsGRP1$^C$ (IC$_{50}$=9.67 μg/ml). On the other hand, the IC$_{50}$ values of the assayed fungal species were all below 58.26 μg/ml except that the causal pathogen of lily leaf blight, *B. elliptica*, exhibited higher tolerance to LsGRP1$^C$ (IC$_{50}$=86.13). According to the IC$_{50}$ values of LsGRP1$^C$ on different bacterial and fungal species, the antimicrobial potency of LsGRP1$^C$ was verified.

TABLE 1

IC$_{50}$ of LsGRP1$^C$ on bacterial and fungal species

| Microorganisms | IC$_{50}$ (μg/ml) |
|---|---|
| Bacterial species[a] | |
| *A. tumefaciens* C58C$^1$ | 71.79 |
| *B. subtilis* 28-4 | 23.32 |
| *E. coli* DH5α | 9.67 |
| *P. syringae* pv. *syringae* 61 | 20.63 |
| *X. campestris* XCP3 | 32.19 |
| Fungal species[b] | |
| *A. brassicicola* Ac1 | 54.80 |
| *B. elliptica* B061 | 86.13 |
| *B. cinerea* B-134 | 58.26 |
| *C. acutatum* HL1 | 17.39 |

[a]Inhibition of bacterial growth (OD$_{600}$ = 0.15).
[b]Inhibition of fungal spore germination at a concentration of 5 × 10$^4$ spores/ml.

EXAMPLE 4

LsGRP1$^C$ Altered Bacterial Morphology and Membrane Permeability

1. Scanning Electron Microscopy

Cover slides pre-coated with 0.1% poly-L-lysine were inoculated with 20 μl bacterial suspension of 10$^8$ cells/ml and kept moist at 28° C. for 12 h. The bacterial colonies attached to the cover slides were treated with 20 μl peptide solution at a concentration of 2.5, 0.25 or 0.025 mg/ml for 2 h. The cells were fixed using 1% glutaraldehyde and washed three times with 150 mM phosphate buffer (pH 7.2), each for 15 min. Next, the cells on slides were coated with 1% OsO$_4$ for 1 h, immersed in 2% uranyl acetate for 30 min, and washed three times with 150 mM phosphate buffer (pH 7.2), each for 15 min. The samples were dehydrated serially using 30%, 50% 70%, 85%, 90%, 95%, 100% and 100% ethanol, each for 30 min, then soaked twice in acetone, each for 30 min, dried in CO$_2$ by a critical point dryer HCP-2 (Hitachi) and coated with gold particles in an ion sputter E101 (Hitachi). The prepared samples were then examined by scanning electron microscope (Inspect S, FEI Company).

2. SYTOX Green Staining

Bacterial suspension of 10$^8$ cells/ml were treated with peptide solution at different concentrations in the presence of 1 μM SYTOX Green (Invitrogen), and incubated at 28° C., 180 rpm for 2 h before observation under Leica DMR fluorescence microscope equipped with a Chroma Endow GFP filter set (BP 450-490 nm, DM 495 nm, BP 500-550 nm). Fungal spore and hyphae were treated with 50 μg/ml peptide solution for 2 h and 16 h, respectively. Then the fungal cells were stained with 1 μg/ml SYTOX Green in the dark for 10 min before observation under Leica DMIL florescent microscope equipped with a Chroma 41012 filter set (BP 460-500 nm, DM 505 nm, LP 510 nm). Sterile deionized water was used instead of peptide solution as a control.

3. Results

Figure 3:
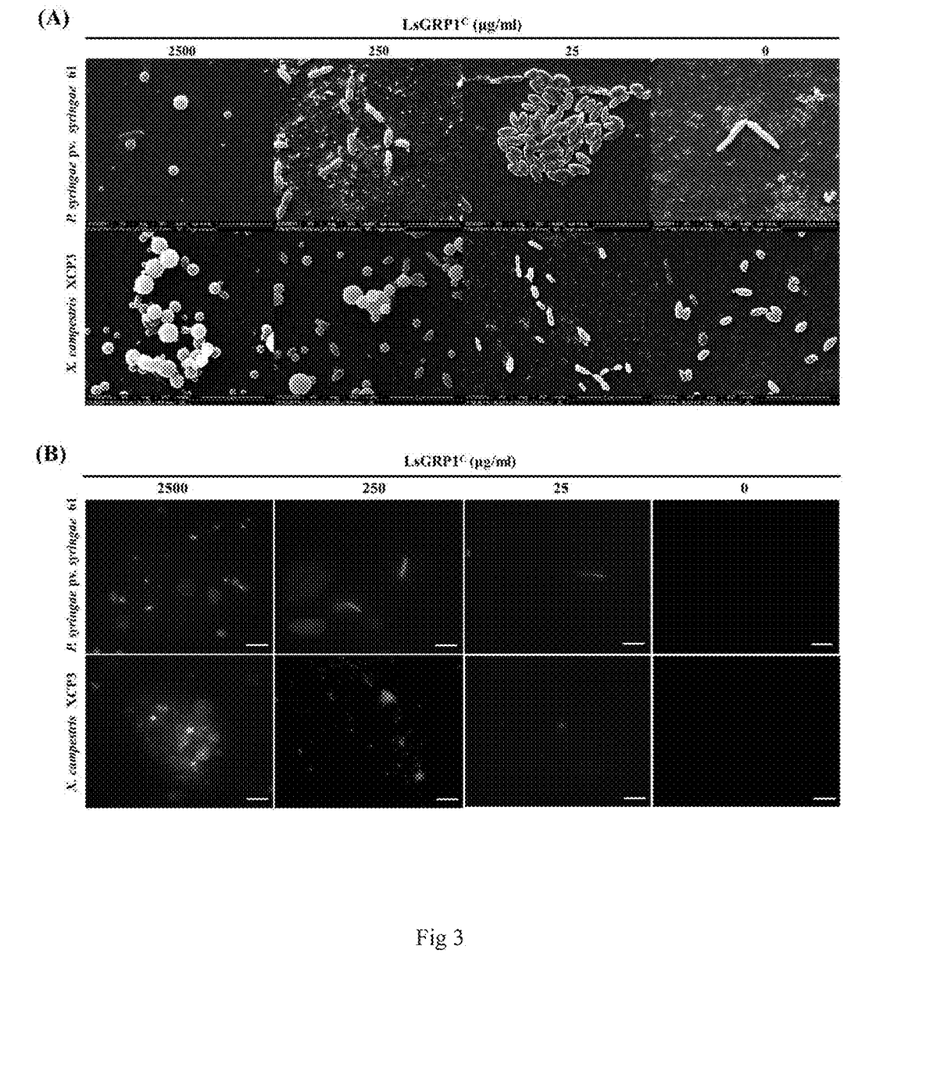
FIG. 3 shows changes in morphology and membrane permeability of bacteria treated with LsGRP1$^C$. (A) Observation of *P. syringae* pv. *syringae* 61 and *X. campestris* XCP3 by scanning electron microscopy post LsGRP1$^C$ treatment. Bar=4 μm (for *P. syringae* pv. *syringae*) or 5 μm (for *X. campestris*). (B) SYTOX Green-stained *P. syringae* pv. *syringae* 61 and *X. campestris* XCP3 post LsGRP1$^C$ treatment. Bar=10 μm.

The effects of LsGRP1$^C$ on the morphology of two bacterial strains, *P. syringae* pv. *syringae* 61 and *X. campestris* XCP3, were examined by scanning electron microscopy. Transformation of a significant number of bacterial cells from rod-shaped to spherical-shaped was observed in both *P. syringae* pv. *syringae* 61 and *X. campestris* XCP3 upon treatment with 2500 μg/ml LsGRP1$^C$ (FIG. 3A). When the concentration of LsGRP1$^C$ treatment was decreased, the cells of *P. syringae* pv. *syringae* 61 and the *X. campestris* XCP3 exhibited a shorten and swollen morphology as compared with the untreated ones, indicating a dose-dependent effect of LsGRP1$^C$.

The morphological change in bacterial cells caused by LsGRP1$^C$ implied the cell membrane of bacteria was damaged by LsGRP1$^C$, and SYTOX Green staining was subsequently used to demonstrate the effect of LsGRP1$^C$ on bacterial membrane. SYTOX Green is impermeable to normal cells but penetrates to damaged cell membranes and causes nuclei florescent. Under fluorescent microscope, fluorescent nuclei were observed in *P. syringae* pv. *syringae* 61 and *X. campestris* XCP3 cells post treatments with LsGRP1$^C$ but not in the water control (FIG. 3B), indicating that LsGRP1$^C$ altered membrane integrity and changed the permeability of bacterial membranes. Moreover, the proportion of SYTOX Green-labeled bacteria positively correlated to the concentrations of LsGRP1$^C$, which was consistent with the morphological changes affected by the treatment with LsGRP1$^C$.

EXAMPLE 5

LsGRP1$^C$ Destroyed Membrane Integrity and Induced Programmed Cell Death-Like Phenomenon in Fungi 1. DAPI Staining Fungal spore and hyphae were treated with 50 μg/ml peptide solution for 2 h and 16 h, respectively. Then the fungal cells were stained with 4',6'-diamidino-2-phenylindole (DAPI) at a final concentration of 1 μg/ml in the dark for 10 min before observation under Leica DMIL florescent microscope equipped with a Leica A filter set (BP340-380 nm, DM 400 nm, LP425 nm). Sterile deionized water was used instead of the peptide solution as a control.

2. H$_2$DCFDA Staining

Fungal spore and hyphae were treated with 50 μg/ml peptide solution for 2 h and 16 h, respectively. Then the fungal cells were stained with 10 μM 2',7'-dichlorodihydrofluorescein diacetate (H$_2$DCFDA) in the dark for 60 min before observation under Leica DMIL florescent microscope equipped with a Chroma 41012 filter set. Sterile deionized water was used instead of peptide solution as a control.

Figure 4:
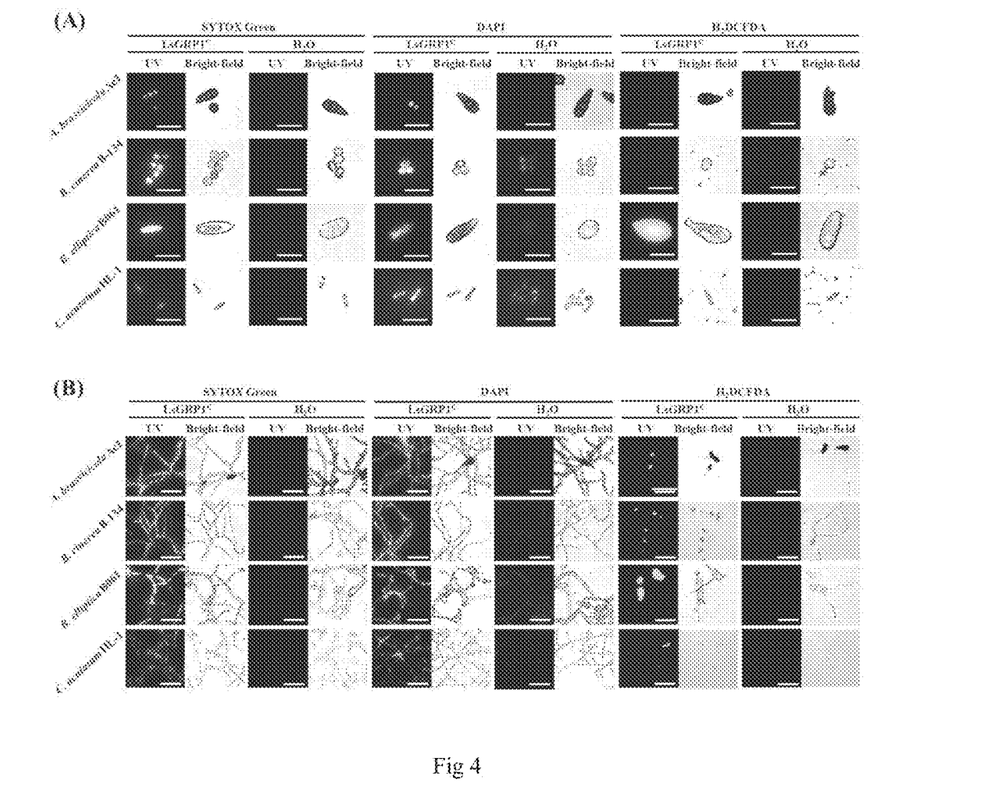

3. Results:

The effects of LsGRP1$^C$ on spores and hyphae of *A. brassicicola* Ac1, *B. cinerea* B-134, *B. elliptica* B061 and *C. acutatum* HL1 were demonstrated (FIG. 4). As observed under light microscope, the spores and hyphae of LsGRP1$^C$-treated fungal species, especially *B. elliptica*, the causal pathogen of lily leaf blight, exhibited abnormal blebbing and shrinkage, and their cytoplasm had a brown, necrotic and granulated appearance. In contrast, fungal spores and hyphae of the control had a smooth, full surface and transparent, homogeneous cytoplasm.

The damages caused by LsGRP1$^C$ to the plasma membrane of spores and hyphae were visualized by SYTOX Green-labeled florescent signal which was not detected in the control, demonstrating that LsGRP1$^C$ affected the membrane integrity of all tested fungal species. Meanwhile, the nuclei of spores and hyphae stained by DAPI showed that LsGRP1$^C$ leaded to fungal nuclear chromatin condensation, a characteristic change of programmed cell death, which did not occurred in the control. In addition, the accumulation of reactive oxygen species (ROS) in the germinating spores pretreated with LsGRP1$^C$ was visualized by H$_2$DCFDA staining but not in the control (FIG. 4B), providing evidence that LsGRP1$^C$ probably induced programmed cell death-like phenomenon in fungi (Sharon et al. 2009). Interestingly, the ROS accumulation triggered by LsGRP1$^C$ was absent in the non-germinating spores of *A. brassicicola*, *B. cinerea*, and *C. acutatum* but present in *B. elliptica* (FIG. 4A), suggesting a faster response of *B. elliptica* to LsGRP1$^C$. To sum up these results, LsGRP is able to destroy the membrane integrity and induce a programmed cell death-like phenomenon in different fungal species.

EXAMPLE 6

Localization of the Acting Target of LsGRP1$^C$

1. Immunofluorescence Microscopy

At first, the fungal hyphae treated with 50 μg/ml LsGRP1$^C$ for 16 h were fixed with 4% formaldehyde in phosphate-buffered saline (PBS, 137 mM NaCl, 2.7 mM KCl, 10 mM Na$_2$HPO$_4$, 2 mM KH$_2$PO$_4$, pH 7.4) for 1 h, treated with 25 mM dithiothreitol in PBS for 20 min, and then digested with 20 mg/ml chitinase in PBS containing 5 μl/ml β-mercaptoethanol for 30 min. Then, the hyphae were immunostained using LsGRP1$^C$ antibody and fluorescein isothiocyanate (FITC)-labeled anti-rabbit IgG antibody (KPL) subsequently. The hyphae were observed under Leica DMIL florescent microscope equipped with a CHROMA 41012 filter set (BP 460-500 nm, DM 505 nm, LP510 nm). LsGRP1$^C$ antibody was prepared from the antiserum of the rabbit immunized with chemically synthetized partial C-terminal sequences of the deduced LsGRP1 (accession number: AAL61539.1) after purified through LsGRP1$^C$ affinity column. Sterile deionized water were used instead of peptide solution as a control.

Figure 5:
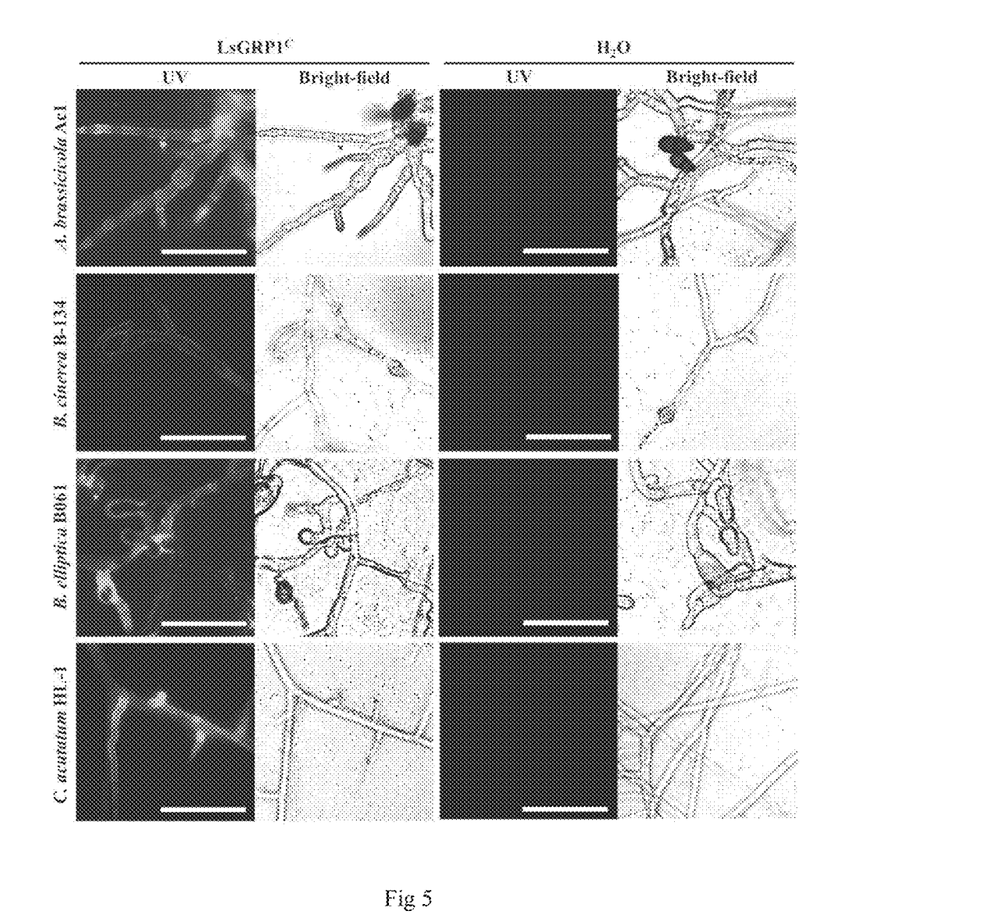
FIG. 5 shows microscopic analysis of immunofluorescence staining for LsGRP1$^C$ in the hyphae of plant fungal pathogens. The fungal hyphae were treated with 50 μg/ml LsGRP1$^C$ for 16 h before the oberservaion. Sterile deionized water was used instead of LsGRP1$^C$ as a control. Bar=25 μm.

2. Results:

To investigate the acting target of LsGRP1$^C$, the fungal hyphae treated with LsGRP1$^C$ were hybridized with LsGRP1$^C$ antibody, and stained with FITC-conjugated anti-rabbit IgG antibody. The fluorescent signals of FITC labeled all LsGRP1$^C$-treated fungal hyphae whereas no signals were observed in the water control (FIG. 5). Since fluorescent signals was mostly localized to the outer layer of hyphae and few of them were found inside the hyphal cells, most LsGRP1$^C$ perhaps bound to fungal cell wall and/or plasma membrane and altered the integrity of fungal membrane; thereby, a few inflow of LsGRP1$^C$ into hyphal cells would occur subsequently.

EXAMPLE 7

LsGRP1-Derived Fusion Protein Abundantly Produced in *E. coli* Host System

1. *E. coli* Expression System

The coding sequences of LsGRP1ΔSP, LsGRP1$^N$, LsGRP1$^G$, and LsGRP1$^C$ were amplified by polymerase chain reaction, and subcloned into vector to generate recombinant construct SUMO-LsGRP1ΔSP, SUMO-LsGRP1$^N$, SUMO-LsGRP1$^G$ and SUMO-LsGRP1$^C$. Next, the recombination plasmids were individually transformed into several *E. coli* strains via heat shock method. The used *E. coli* strains included BL21(DE3), C41(DE3), C43(DE3), C41(DE3) pLysS, and C43(DE3) pLysS. Then transformed *E. coli* were cultured in 3 ml LB with 50 ppm kanamycin broth at 37° C., 175 rpm for 12 h, sub-cultured to 300 ml LB broth with 50 ppm kanamycin at 37° C., 175 rpm, for 2-3 h, then induced with 1 mM isopropyl β-D-1-thiogalactopyranoside (IPTG) for 3 h. Finally, *E. coli* cells were collected by centrifugation at 7,500×g, boiling in 50 μl 1× Laemmli sample buffer, and the total cell lysate was assayed by western blot analysis applied with His-tag antibody to detect the yield of LsGRP1-derived fusion proteins.

Figure 6:
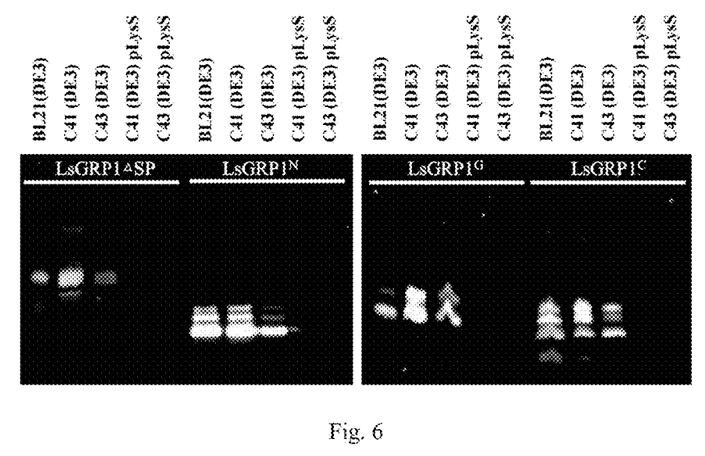
FIG. 6 shows LsGRP1$^N$, LsGRP1$^G$ and LsGRP1$^C$ being fused with 6× His tag and partial SUMO (SEQ ID NO:4), stably expressed by *E. coli*.

2. Results:

LsGRP1ΔSP, LsGRP1$^N$, LsGRP1$^G$, and LsGRP1$^C$ fusing with an N-terminal partner of 6× His (histidine)-tag and partial SUMO (SEQ ID NO:4) expressed by five different *E. coli* strains, including BL21(DE3), C41(DE3), C43(DE3), C41 (DE3) pLysS, and C43(DE3) pLysS, then the total lysates of these bacterial cells were individually collected at 3 h post IPTG induction and analyzed by western blotting with His-tag antibody. Among them, *E. coli* strains C41(DE3) and BL21(DE3) were most suitable for the production of these fusion protein (FIG. 6).

EXAMPLE 8

LsGRP1$^C$ Fusion Protein Conducting Pathogen Death

1. Production of Fusion Protein 6× His-SUMO-LsGRP1$^C$

Fusion protein 6× His-SUMO-LsGRP1$^C$ was expressed in *E. coli* C41(DE3) which was induced by 1 mM IPTG for 6 h, purified by His-tag purification resin, desalted by dialysis in deionized water, concentrated by lyophilization, then performed Bradford protein assay.

2. SYTOX Green Staining and DAPI/and TUNEL Assay

*B. elliptica* hyphae were treated with 150 μg/ml 6× His-SUMO-LsGRP1$^C$ solution at 20° C. for 20 h, then performed SYTOX Green, DAPI and TUNEL stainings Sterile deionized water (H$_2$O) was used instead of 6× His-SUMO-LsGRP1$^C$ as a control.

Figure 7:
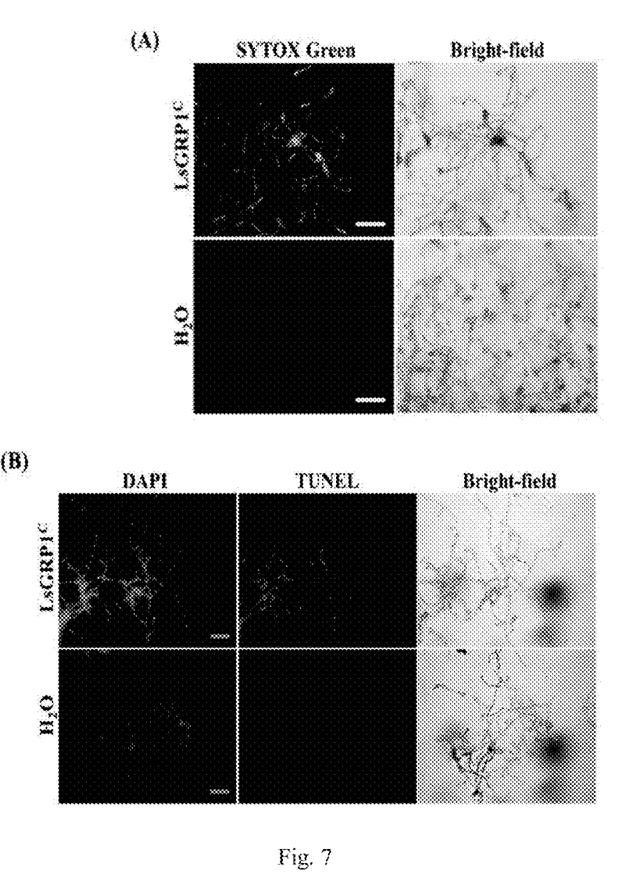
FIG. 7 shows LsGRP1$^C$ fusion protein conducting *Botrytis elliptica* membrane permeabilization and cell death, assayed by SYTOX Green staining and DAPI/TUNEL assays.

3. Results:

Membrane permeability and chromatin condensation/nuclear DNA fragmentation of treated *B. elliptica* hyphae were assayed by SYTOX Green staining (FIG. 7A, Bar=200 μm) and DAPI/TUNEL assays (FIG. 7B, Bar=200 μm), respectively. Since SYRTOX Green-stained permeable cells and DAPI/TUNEL-labeled chromatin condensation/nuclear DNA fragmentation were observed in the hyphae of LsGRP1$^C$ fusion protein treatment but not in water control, LsGRP1$^C$ fusion protein conducting fungal membrane permeabilization and programmed cell death is considered. Bar=200 μm.

EXAMPLE 9

LsGRP1$^C$ Fusion Protein showing better Effect to Alter Membrane Integrity than LsGRP1 Fusion Protein 1. Production of Fusion Proteins 6× His-SUMO-LsGRP1$^C$ and 6× His-SUMO-LsGRP1

Fusion proteins 6× His-SUMO-LsGRP1$^C$ and 6× His-SUMO-LsGRP1 were individually expressed by *E. coli* C41 (DE3) which were induced with 1 mM IPTG for 6 h, purified by His-tag purification resin, desalted by dialysis in deionized water, concentrated by lyophilization, and performed Bradford protein assay.

2. SYTOX Green Staining

*P. syringae* TM2 of 1.6×10$^6$ cells/ml were treated with fusion protein solutions at 100 μg/ml in the presence of 2 μM SYTOX Green, and incubated at 28° C., 180 rpm for 2 h. Then, membrane permeabilization and viable count of the treated bacterial cells was examined under a Leica DMR fluorescence microscope equipped with a Chroma Endow GFP filter set and plating out method. Sterile deionized water was used instead of fusion protein solution as a control.

Figure 8:
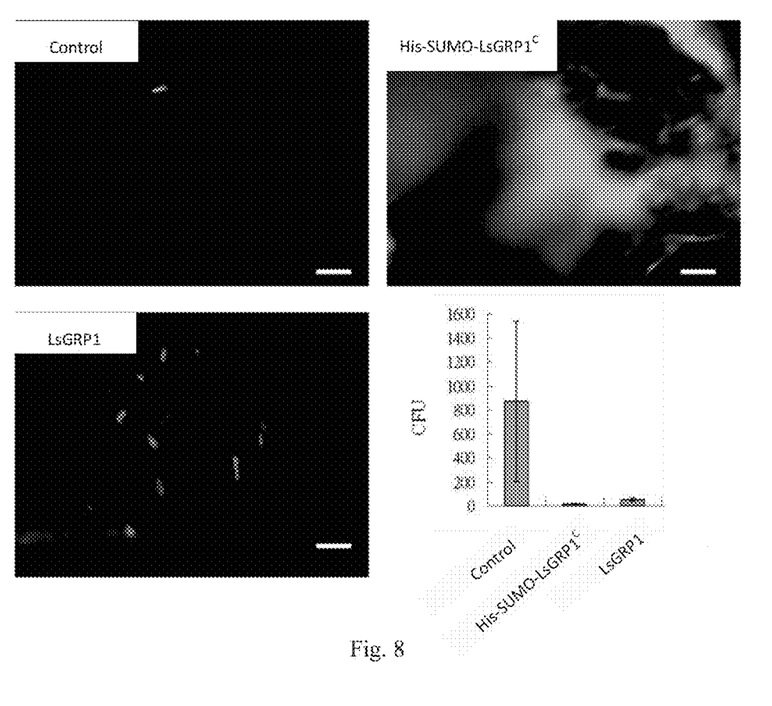
FIG. 8 shows LsGRP1$^C$ fusion protein conducting better efficiency to alter membrane integrity than full length LsGRP1$^C$ fusion protein.

3. Results:

The occurrence of membrane permeabilization of *P. syringae* TM2 visualized by SYTOX Green staining was most abundant in 6× His-SUMO-LsGRP1$^C$ treatment, fewer in 6× His-SUMO-LsGRP1 treatment, and hardly seen in sterile deionized water control (FIG. 8, Bar=10 μm). This result revealed that 6× His-SUMO-LsGRP1$^C$ conducted more permeabilization in membrane as compared with 6×His-SUMO-LsGRP1, and meanwhile, sterile deionized water treatment showed almost no effect on membrane permeabilization.

EXAMPLE 10

LsGRP1$^C$ Fusion Protein showing Antimicrobial Activity on Lily Leaves

1. Production of Fusion Proteins 6× His-SUMO-LsGRP1$^C$ and 6× His-SUMO

Fusion protein 6× His-SUMO-LsGRP1$^C$ and fusion protein 6× His-SUMO were expressed in *E. coli* C41(DE3) after the induction with 1 mM IPTG for 6 h, purified by His-tag purification resin, desalted by dialysis in deionized water, concentrated by lyophilization, and quantitated with Bradford protein-binding assay.

2. Antimicrobial Assay on Lily Leaves

The middle leaves of 7 week-old *Lilium* cv. Stargazer were infiltrated with 6× His-SUMO-LsGRP1$^C$ solution of 100 μg/ml and detached at 2 h after protein infiltration. The detached leaves were dropped with 10 μl *B. elliptica* spore suspension (5×10$^4$ spores/ml), kept moisture, and incubated at 20° C. for 24 h. Then the leaves were stained with 1 μg/ml trypan blue and observed under a light microscopy. Fusion protein 6× His-SUMO expressed by *E. coli* C41(DE3) was used instead of 6× His-SUMO-LsGRP1$^C$ as a control.

Figure 9:
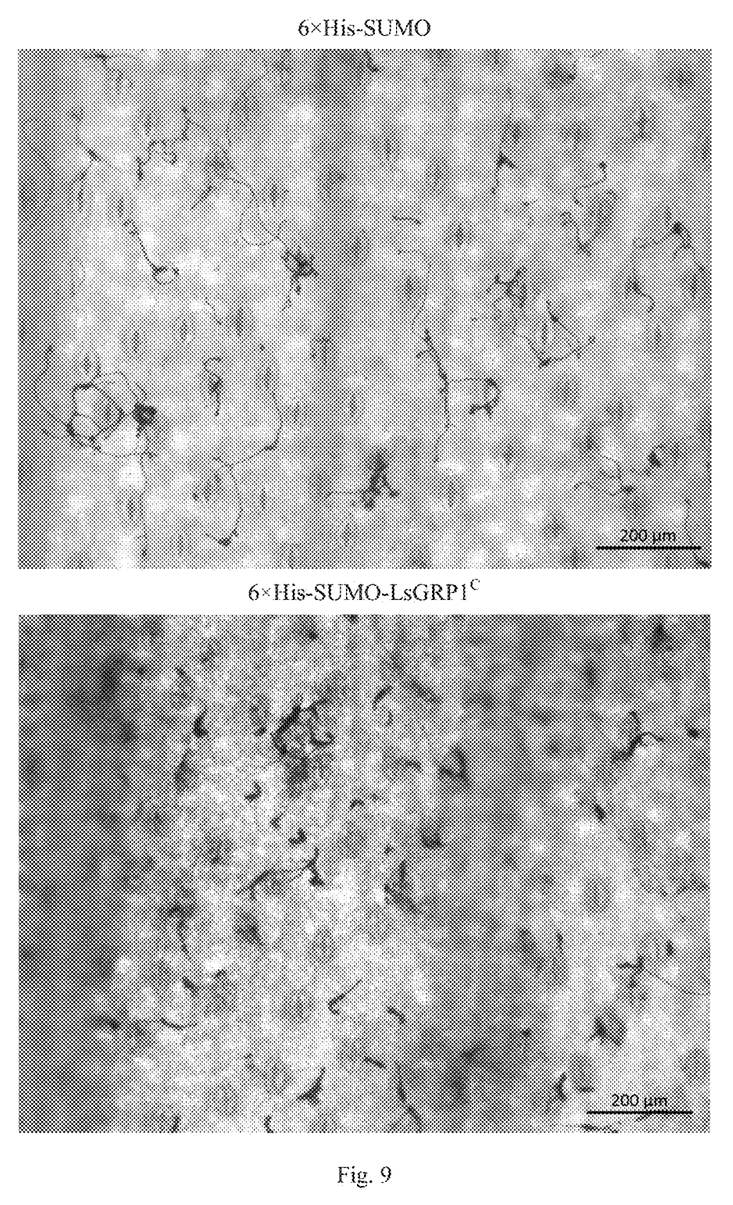
FIG. 9 shows antimicrobial activity of LsGRP1$^C$ fusion protein on lily leaves, inhibiting spore germination and hyphae growth of *Botrytis elliptica* membrane at 24 hours post inoculation.

3. Results:

The effect of 6× His-SUMO-LsGRP1$^C$ on spore germination and hyphae growth of *B. elliptica* in planta was observed at 24 h post inoculation. As compared with the leaves infiltrated with 6× His-SUMO solution, fewer germinating spores and shorter hyphae were found on the leaves infiltrated with 6× His-SUMO-LsGRP1$^C$ solution (FIG. 9), indicating 6× His-SUMO-LsGRP1$^C$ in lily leaves conducted suppression effect on *B. elliptica* infection.

EXAMPLE 11

LsGRP1$^C$ Suppressing Lesion Development on Plant Leaves

1. Disease Suppression Assay

The synthetic LsGRP1$^C$ solutions of 2.5, 0.25 or 0.025 mg/ml were used. LsGRP1$^C$ solution was dropped onto the surface of cabbage leaves. Meanwhile 5 μl spore suspension of *A. brassicicola* (2×10$^5$ conidia/ml), a fungal pathogen of cabbage black spot, was mixed with LsGRP1$^C$ solution. In addition, fungal spore suspension was deposited before or after LsGRP1$^C$ application. On the other hand, synthetic LsGRP1$^C$ solution was dropped onto strawberry flowers, and then mixed with spore suspension of *B. cinerea* (2×10$^5$ conidia/ml). Similarly, synthetic LsGRP1$^C$ solution was dropped onto tomato leaves, and then mixed with bacterial suspension of *P. syringae* (10$^7$ CFU/ml). Sterile water was used instead of LsGRP1$^C$ solution as a control. Lesion development was examined visually.

2. Results:

(1) LsGRP1$^C$ Suppressing Lesion Development of Cabbage Black Spot

Figure 10:
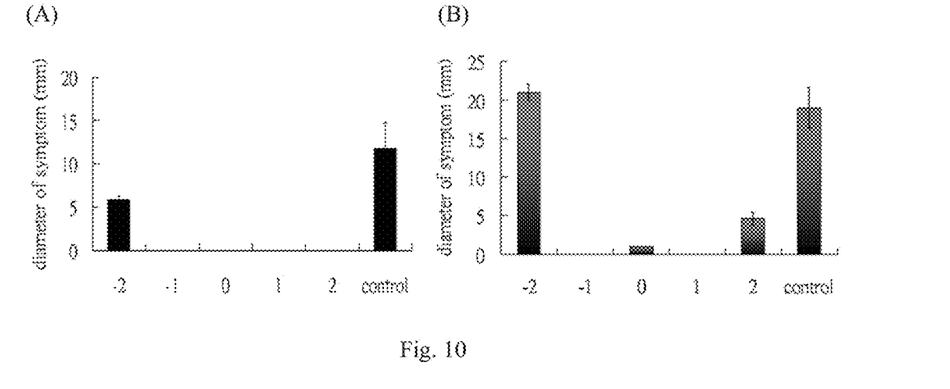
FIG. 10 shows treating LsGRP1$^C$ before/after inoculation suppressing lesion development of cabbage black spot on leaves 7 days post inoculation in (A) 0.25 mg/ml and (B) 0.025 mg/ml, respectively.

Fungal inoculation was two days (−2) or one day (−1) before treatment besides at same time of the treatment. Fungal inoculation was also performed two day (2) or one day (1) after treatment. The figure shows the diameter of lesion symptoms on leaves 7 days after fungal inoculation: (FIG. 10A) 0.25 mg/ml LsGRP1$^C$, (FIG. 10B) 0.025 mg/ml LsGRP1$^C$. Lesion development could be inhibited by 0.25 mg/ml LsGRP1$^C$ treatment at the same time of fungal inoculation or 1-2 day before/after fungal inoculation. However, this suppression effect did not occur when fungal inoculation at 2 days before 0.025 mg/ml LsGRP1C treatment.

(2) LsGRP1$^C$ can Suppress Lesion Development of Gray Mold Disease

Figure 11:
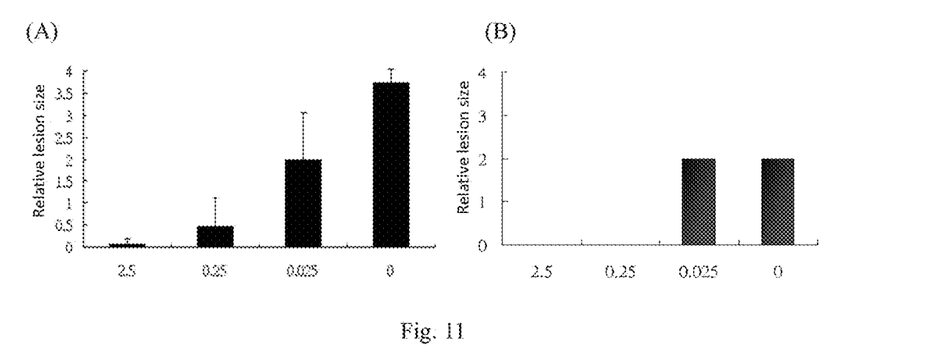
FIG. 11 shows treating LsGRP1$^C$ suppressing lesion development of gray mold on leaves (A) 3 days and (B) 9 days post inoculation in different concentration.
Figure 12:
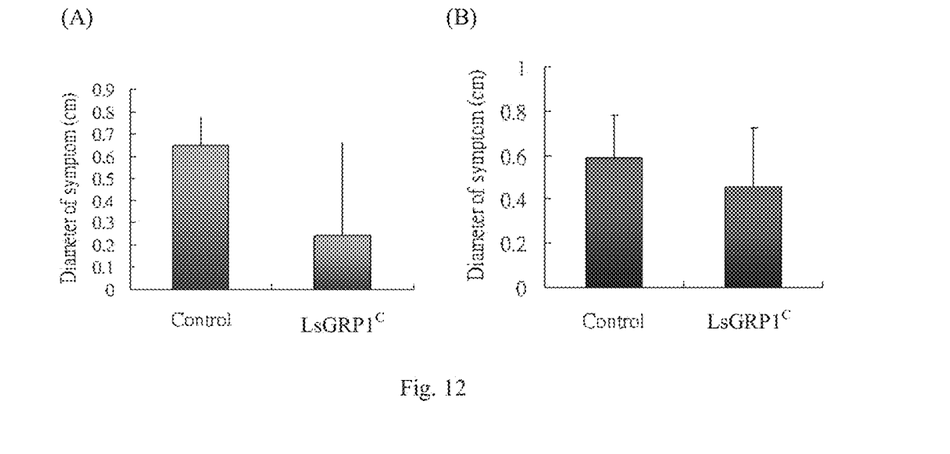
FIG. 12 shows treating LsGRP1$^C$ suppressing lesion development of tomato bacterial peaf spot on leaves 6 days post inoculation in (A) 0.25 mg/ml and (B) 0.025 mg/ml, respectively.

Synthetic LsGRP1$^C$ solution (1 μl each) was dropped onto strawberry flowers, then mixed with 1 μl spore suspension of *B. cinerea*. FIG. 11A shows the lesion development 3 days after fungal inoculation. LsGRP1$^C$ solution (5 μl each) was dropped onto orchid flowers, then mixed with 5 μl spore suspension of *B. cinerea*. FIG. 11B shows the lesion development 9 days after fungal inoculation. These results indicated that lesion development of fungal diseases as strawberry and orchid gray mold could be suppressed by LsGRP1$^C$ treatment in a dosage-dependent manner (3) LsGRP1$^C$ Suppressing Lesion Development of Bacterial Leaf Spot in Tomato LsGRP1$^C$ solution (10 μl each) was dropped onto wounded tissues of tomato leaves, mixed with 10 μl bacterial suspension (10$^7$ CFU/ml) of pathogenic *P. syringae*, and then lesion development was examined 6 days after bacterial inoculation. FIG. 12 showed that LsGRP1$^C$ of (A) 0.25 mg/ml and (B) 0.025 mg/ml could inhibit lesion development of bacterial leaf spot in tomato.

Conclusions

All the prediction servers used in this invention suggested that an antimicrobial activity mainly conferred by LsGRP1$^C$. However, in practical assays, LsGRP1$^N$, LsGRP1$^G$ and LsGRP1$^C$ of 2500 μg/ml exhibited high inhibitory activities on both Gram (+) and Gram (−) bacteria as compared with the BSA control, suggesting that not only the cysteine-rich C-terminal region of LsGRP1 protein but also other regions were toxic to bacteria. Furthermore, the low IC$_{50}$ value of LsGRP1$^C$ on E. coli DH5α (9.67 µg/ml) indicated that E. coli was highly sensitive to the expressed LsGRP1 bearing LsGRP1$^C$ region, and the unsuccessful previous production of LsGRP1 in E. coli was due to the antimicrobial activity conferred by the C-terminal cysteine region and also other parts of LsGRP1.

Although the three LsGRP1-derived peptides effectively inhibited all of the bacterial species investigated (81-100% inhibition), only LsGRP1$^C$ inhibited all the fungal strains investigated to a high degree, which was consistent with the predicted antimicrobial activity for this peptide by AMP prediction servers. The antimicrobial activity and spectrum of LsGRP1$^C$ were further demonstrated by the low $IC_{50}$ values on various kinds of bacterial and fungal species. The combined traits of effective inhibitory activity and broad antimicrobial spectrum of LsGRP1$^C$ suggested that this peptide could act on certain common targets or has diverse effects on microbial physiology. In SYTOX Green staining assay, LsGRP1$^C$ was shown to disrupt the membrane integrity of both bacterial and fungal cells. Moreover, LsGRP1$^C$ was localized to the cell surface of fungal hyphae providing evidence of the cell wall and/or plasma membrane location of the acting target of LsGRP1$^C$. In addition to membrane permeabilization, LsGRP1$^C$ caused nuclear chromatin condensation and ROS accumulation in four treated fungal species, indicating that LsGRP1$^C$ would induce fungal programmed cell death. Therefore, LsGRP1$^C$ may not only directly alter membrane integrity in both bacterial and fungal microorganisms, but also induce programmed cell death-like phenomenon at least in some fungi. The antimicrobial activity of LsGRP1$^C$ might be a result of multiple effects on microorganisms.

According to many examples and the results, LsGRP1$^C$ shows best antimicrobial activity toward bacterium as well as fungus in fragments of LsGRP1 protein. However, due to the difficulty of extracting LsGRP1 from lily plants, LsGRP1$^C$ could only be obtained by chemical synthesis or purification of LsGRP1$^C$ fusion protein expressed by microbe, such as E. coli. The example shows LsGRP1$^C$ fusion protein can be produced by E. coli—system; meanwhile, the fusion protein demonstrates no less antimicrobial activity than original LsGRP1$^C$. Dosage of treatment is also defined. Obviously although LsGRP1 is a naturally occurring protein, the amount in plant is extremely low and cannot effectively defend from infection. In contrast, the method of treatment of current invention prescribes a dosage which is not the naturally occurring concentration and much more than natural occurring concentration, so the efficacy of suppression is significant.

In this invention, a novel AMP LsGRP1$^C$ derived from a defense-related protein of lily was demonstrated; meanwhile, LsGRP1$^C$ fusion protein produced by E. coli exhibiting better inhibition activity as compared with LsGRP1 fusion protein, indicating the antimicrobial ability of LsGRP1$^C$ is stronger than LsGRP1. These results revealed that LsGRP1$^C$ obtained by chemical synthesis and the purification of LsGRP1$^C$ fusion protein produced by microbe is a potential AMP in practical application.

What is claimed is:

1. A method of controlling or combating microbial organisms, comprising applying an effective dose of an antimicrobial composition, LsGRP 1$^c$ (SEQ ID NO: 3), to a bacterium or a fungus, wherein the bacterium is selected from the group consisting of *Agrobacterium tumefaciens, Bacillus subtilis, Escherichia coli, Dickeya chrysanthemi, Pseudomonas syringae pv. syringae*, and *Xanthomonas campestris*, wherein the fungus is selected from the group consisting of *Alternaria brassicicola, Botrytis cinerea, Botrytis elliptica, Colletotrichum acutatum*, and *Colletotrichum gleosporioides*, wherein LsGRP1$^c$ (SEQ ID NO:3) inhibits spore germinations on *Alternaria brassicicola, Botrytis cinerea, Botrytis elliptica, Colletotrichum acutatum*, and *Colletotrichum gleosporioides*, wherein the effective dosage of LsGRP 1$^c$ (SEQ ID NO: 3) ranges from 0.01 mg/ml to 2.5 mg/ml.

2. The method of claim 1, wherein the antimicrobial composition comprises pharmaceutically acceptable vehicles, excipients, diluents, and adjuvants.

3. The method of claim 1, wherein the peptide is produced through microbe expression system.

4. The method of claim 1, wherein the peptide is fused to a peptide tag.

* * * * *

SEQUENCE LISTING

```
<160> NUMBER OF SEQ ID NOS: 4

<210> SEQ ID NO 1
<211> LENGTH: 26
<212> TYPE: PRT
<213> ORGANISM: Lilium 'Stargazer'

<400> SEQUENCE: 1

Gly Arg Glu Leu Ala Glu Glu Thr Lys Glu Asn Thr Glu Lys Arg Ala
1               5                   10                  15

Thr Glu Ala Gly Val Ala Asp Gln Lys Tyr
            20                  25

<210> SEQ ID NO 2
<211> LENGTH: 51
<212> TYPE: PRT
<213> ORGANISM: Lilium 'Stargazer'

<400> SEQUENCE: 2

Gly Gly Gly Tyr Asn Asn Gly Gly Gly Tyr Pro Gly Gly Gly Gly Gly
1               5                   10                  15

Tyr His Asn Gly Gly Gly Tyr Pro Gly Gly Gly Gly Gly Tyr Pro Gly
            20                  25                  30

Gly Gly Gly Gly Tyr Pro Gly Gly Gly Gly Tyr His Asn Gly Gly
        35                  40                  45

Gly Gly Gly
    50

<210> SEQ ID NO 3
<211> LENGTH: 38
<212> TYPE: PRT
<213> ORGANISM: Lilium 'Stargazer'
```

```
<400> SEQUENCE: 3

Arg Cys Tyr Asn Gly Cys Cys Arg Arg Gly Tyr Tyr Gly Gly Cys Arg
1               5                   10                  15

Cys Cys Ala His Pro Asp Glu Ile Pro Asp Pro Glu Tyr Arg Ala Glu
            20                  25                  30

Pro Ala Tyr Gly His Pro
        35

<210> SEQ ID NO 4
<211> LENGTH: 98
<212> TYPE: PRT
<213> ORGANISM: Saccharomyces cerevisiae

<400> SEQUENCE: 4

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
            35                  40                  45

Met Glu Ala Phe Ala Lys Arg Gln Gly Lys Glu Met Asp Ser Leu Arg
        50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly
```